United States Patent
Cook et al.

(10) Patent No.: US 6,258,097 B1
(45) Date of Patent: Jul. 10, 2001

(54) HEAD CENTER INSTRUMENT AND METHOD OF USING THE SAME

(75) Inventors: Kevin Cook; Paul Hickey, both of Warsaw, IN (US); John D. Cooper, Bilogla Plateau (AU)

(73) Assignee: Bristol-Myers Squibb Co, New York, NY (US)

( * ) Notice: Subject to any disclaimer, the term of this patent is extended or adjusted under 35 U.S.C. 154(b) by 0 days.

(21) Appl. No.: 09/586,083

(22) Filed: Jun. 2, 2000

(51) Int. Cl.[7] ................................................. A61B 17/56
(52) U.S. Cl. ............................................. 606/91; 606/102
(58) Field of Search ........................... 623/22.12; 606/91, 606/102, 87

(56) References Cited

U.S. PATENT DOCUMENTS

| | | | | |
|---|---|---|---|---|
| 5,141,512 | * | 8/1992 | Farmer et al. | 606/91 |
| 5,290,315 | * | 3/1994 | DeCarlo, Jr. | 623/22.12 |
| 5,423,827 | * | 6/1995 | Mumme et al. | 606/87 |
| 5,607,431 | * | 3/1997 | Dudasik et al. | 606/102 |
| 5,885,297 | * | 3/1999 | Matsen, III | 606/102 |
| 5,916,220 | * | 6/1999 | Masini | 606/87 |
| 5,954,720 | * | 9/1999 | Collaro | 606/91 |
| 6,024,746 | * | 2/2000 | Katz | 606/87 |
| 6,096,043 | * | 8/2000 | Techiera | 606/87 |
| 6,173,200 | * | 1/2001 | Cooke et al. | 606/87 |

FOREIGN PATENT DOCUMENTS

1706589 * 2/1992 (SU) .................................. 606/102

* cited by examiner

Primary Examiner—Paul J. Hirsch

(57) ABSTRACT

An orthopaedic instrument for comparing post-surgical joint geometry to pre-surgical joint geometry. The instrument has a head chuck which can be secured to the ball of a ball joint, and an arm having reference indicia thereon. Markings indicative of the pre-surgical joint geometry are made on the bone with reference to the center of the ball. After replacement with a prosthetic ball, the post-operative geometry is verified by securing the head chuck to the prosthetic ball, and comparing the location of the bone markings against the reference indicia on the arm. As needed, adjustments are made in the prosthetic components.

23 Claims, 5 Drawing Sheets

HEAD CENTER INSTRUMENT AND METHOD OF USING THE SAME

BACKGROUND OF THE INVENTION

1. Field of the Invention

The present invention relates to instruments used in performing orthopaedic surgery, and more particularly, to an instrument used to aid in properly positioning a prosthetic ball on a bone in a ball joint, such as the replacement of a femoral head during hip replacement surgery.

2. Description of the Related Art

When performing joint reconstruction surgical procedures, such as hip replacement surgery, it is important that the pre-surgical geometry of the bone structure be replicated in the post-surgical structure, including prosthetic implants. Duplicating the geometric relationships maintains the natural joint biomechanics, ensuring proper joint and soft tissue balancing forces. If, during hip replacement surgery, for example, the center of the femoral prosthetic implant is moved slightly to a position different from the original position of the natural femoral head, the result can be higher joint forces, weak abductor muscles and overall joint instability. Even relatively slight mis-positioning of the prosthetic joint component can lead to a negative surgical result.

While planning the procedure, x-rays can be used for pre-surgical templating, to assist in determining the apparent appropriate implant size, head offset and head neck length necessary to reestablish the joint biomechanics. However, while pre-surgical, two dimensional templating is useful in selecting the proper prosthetic implant, and for establishing the proper fit and positioning of the implant during surgery, even with careful and deliberate pre-surgical planning and calculation, it is common to also perform intra-operative verification of the natural joint geometry and of the geometry resulting after implant, to ensure proper function of the joint post-surgically.

It is known during hip surgery to determine the natural offset and neck length of the femoral head by measurement. Offset can be measured from the tip of the greater trochanter to the center of the femoral head. Neck length can be measured from the tip of the lesser trochanter to the center of the femoral head. When selecting the prosthetic components, an attempt is made to duplicate as closely as possible the same measurements taken with respect to the prosthetic devices, after the provisional implants have been positioned. While placing the prosthetic components, the measurements are repeated, to verify concurrence between the pre-surgical and post-surgical geometry of the joint, by reestablishing the measured values in the joint after implant.

Even with advance planning, selection of the appropriate modular head and neck components of the prosthetic implant can require the trial of several components, with the proper components being identified only after repeated measurements of the several components tried. Various measuring calipers, frames or positioning jigs have been suggested as ways to increase the accuracy in duplicating the pre-surgical geometry of the joint after implanting prosthetic components.

What is needed is an orthopaedic instrument, and a surgical procedure for use of the instrument, which can be used to precisely and accurately duplicate, in the post-surgical geometry, the geometry that existed in the joint, pre-surgically.

SUMMARY OF THE INVENTION

The present invention provides an orthopaedic instrument, and a procedure for use of the instrument, for duplicating the pre-surgical joint geometry of a ball joint in the geometry of the joint post-surgically, by establishing markings relating to the head center position of the natural femoral head, against which markings the head center of the prosthetic femoral head can be compared during surgery.

The invention comprises, in one form thereof, an orthopaedic instrument for establishing reference markings indicative of the pre-surgical joint geometry relative to the center of a ball in a ball joint, and for evaluating the post-surgical geometry relative to the head center of a prosthetic implant. The instrument includes a head chuck, with a plurality of locator devices adjustably retained by the head chuck. The locator devices are adapted to at least partially receive and engage the ball. An adjustment means associated with the head chuck and with the plurality of locator devices is used to bring each of the plurality of locator devices into engagement with the ball, for securing the position of the instrument head chuck relative to the ball. An orientation arm extends outwardly away from the head chuck and includes reference indicia for establishing and comparing bone markings.

In a second aspect thereof, the invention comprises a surgical procedure for comparing the neck angle and length of a prosthetic ball component of a ball joint to the neck angle and length of the natural ball. The procedure includes providing an instrument having a head chuck adapted to be secured in position relative to the natural ball of a ball joint and to the ball of a prosthetic implant; providing an arm on the instrument extending from the head, the arm being of sufficient length to reach a bone surface remaining after reduction; providing a plurality of reference indicia on the arm of the instrument; exposing the ball component of the ball joint, positioning the instrument over the ball, securing the position of the orientation arm relative to the center of the ball; establishing bone markings relative to selected ones of the plurality of indicia on the orientation arm; removing the instrument; replacing, surgically, the natural ball of the ball joint with a prosthetic ball component; securing the orientation arm relative to the center of the prosthetic ball; comparing the bone markings to the selected ones of the plurality of indicia on the orientation arm with respect to which the bone markings were made; and adjusting, as necessary, the neck length and angle of the prosthetic ball to match the bone markings against the selected ones of the plurality of indicia against which the bone markings were made.

In another aspect thereof, the invention comprises an orthopaedic instrument having a head chuck including a cylindrical body and a cap rotatably secured in the body. An orientation arm extends radially outwardly from the body. A plurality of locator devices are associated with the head chuck for securing the head chuck relative to the center of a ball component of a ball joint. Indicia on the orientation arm are reference points for making and comparing bone markings.

In still another aspect of the present invention, a method is provided for replacing a femoral head. The method includes exposing the femoral head surgically, securing a reference gauge against the posterior femur relative to the femoral head center; creating reference markings on the posterior femur; removing the reference gauge; replacing the femoral head with a prosthetic femoral head; re-securing the reference gauge against the posterior femur relative to the center of the prosthetic femoral head; comparing the bone markings against the reference gauge; and adjusting the prosthetic femoral head to achieve a relationship between the bone markings and the reference gauge similar to the relationship when the bone markings were made.

An advantage of the present invention is an instrument for accurately duplicating natural joint geometry following surgery to replace the ball of a ball joint, through the intra-operative verification of the prosthetic head center location relative to the head center location in the natural joint.

Another advantage of the present invention is an instrument that is simple and easy to use for comparing the natural femoral head neck length and neck angle to the prosthetic femoral head neck length and neck angle during surgery to replace a femoral head.

A further advantage is a surgical procedure to aid a surgeon in restoring proper joint biomechanics when performing joint replacement surgery.

BRIEF DESCRIPTION OF THE DRAWINGS

The above-mentioned and other features and advantages of this invention, and the manner of attaining them, will become more apparent, and the invention will be better understood, by reference to the following description of an embodiment of the invention, taken in conjunction with the accompanying drawings, wherein:

FIG. 6 is an elevational view of a prosthetic femoral head, showing in broken lines a manner of increasing femoral neck length.

Figure 1:
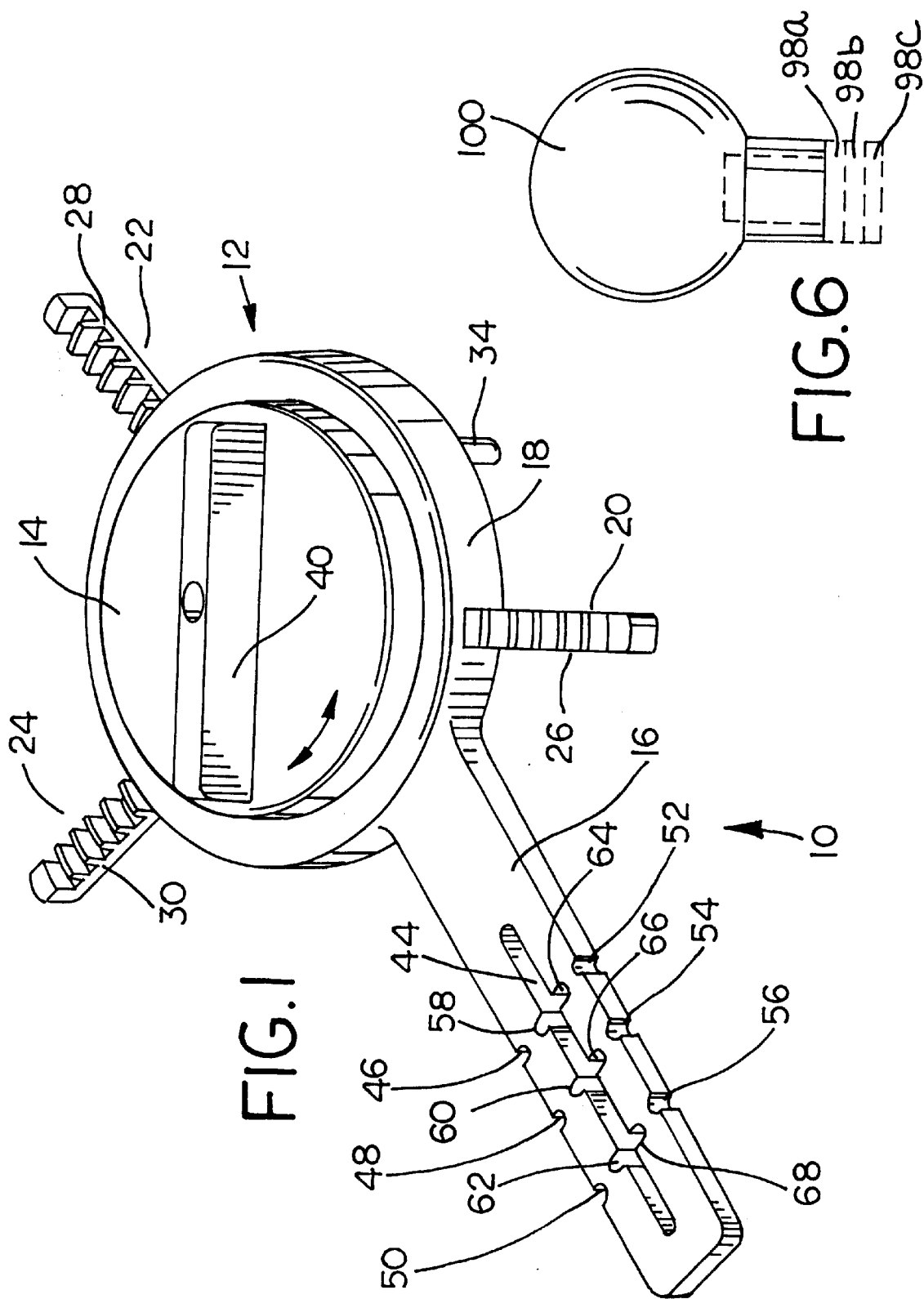
FIG. 1 is a perspective view of an orthopaedic head center instrument according to the present invention.

Corresponding reference characters indicate corresponding parts throughout the several views. The exemplification set out herein illustrates one preferred embodiment of the invention, in one form thereof, and such exemplification is not to be construed as limiting the scope of the invention in any manner.

DETAILED DESCRIPTION OF THE PREFERRED EMBODIMENT

Referring now to the drawings, and particularly to FIG. 1 thereof, an orthopaedic head center instrument 10 of the present invention is shown. Instrument 10 is used to establish landmarks relating to the geometric orientation of a ball component in a ball joint, and for gauging and adjusting the position of a prosthetic implant to duplicate the pre-surgical geometry in the post-surgical geometry. The present invention will be described with respect to landmarking the posterior portion of the proximal end of a femur during hip replacement surgery. It should be understood that the present invention also may be used for the replacement of other joint components as well, and particularly other ball joint components, such as, for example, on the humerus.

Instrument 10 includes a head chuck 12 having a rotatable cap 14 rotatably secured therein. An orientation arm 16 extends radially from head chuck 12. Head chuck 12 includes a cylindrical body 18 adapted to slidingly receive a plurality of locator devices 20, 22 and 24. In a preferred construction, locator devices 20, 22 and 24 are spaced 120 apart from each other around head chuck 12.

Each of locator devices 20, 22 and 24 includes, respectively, a rack element 26, 28 and 30 extending radially through body 18, and slidingly received in body 18. Locator pins 32, 34 and 36 extend from the outer ends of rack elements 26, 28 and 30, respectively, locator pins 32, 34 and 36 being disposed on the distal ends of rack elements 26, 28 and 30, inwardly of body 18, and oriented downwardly from rack elements 26, 28 and 30 with respect to cap 14.

Figure 3:
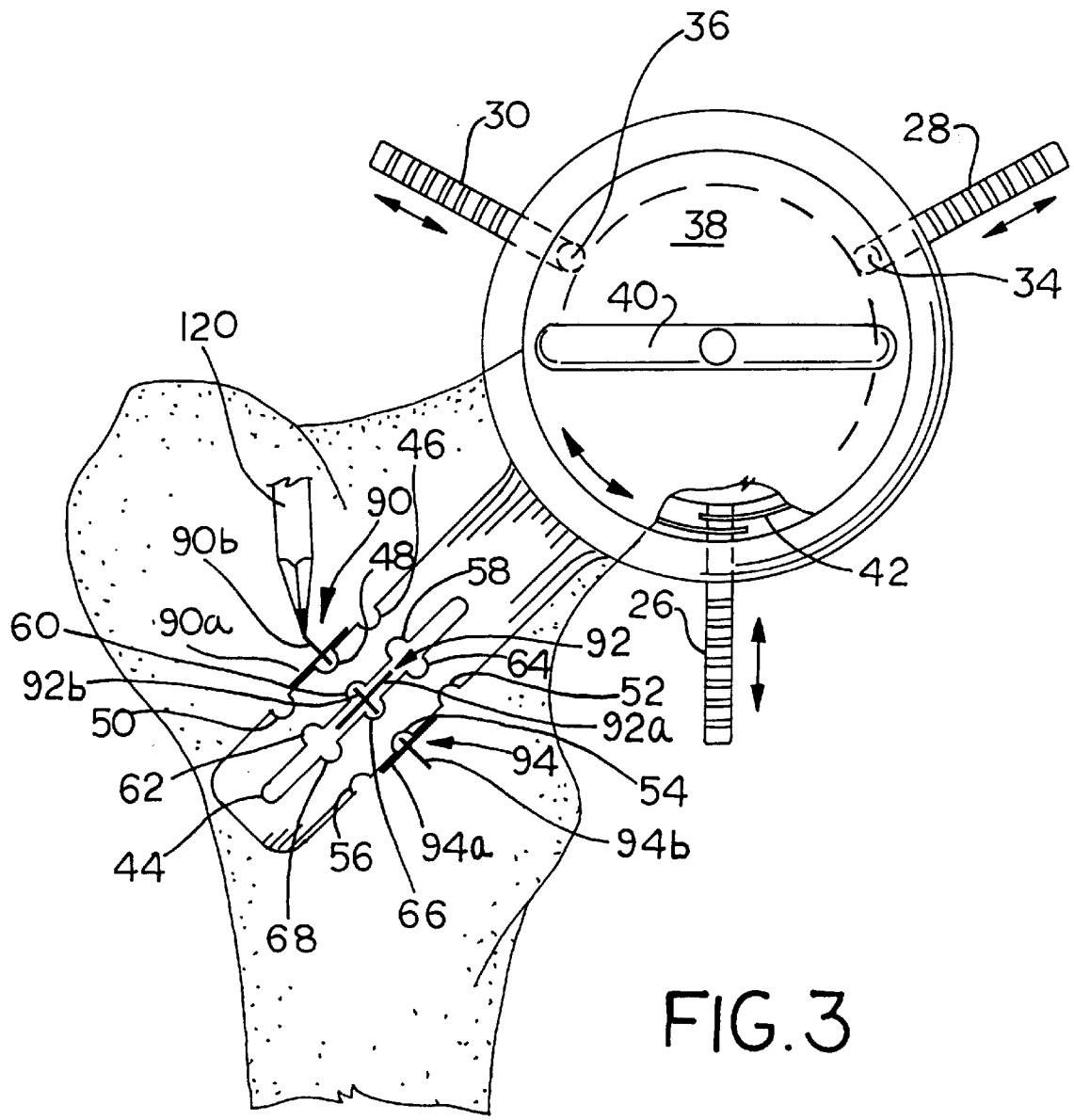
FIG. 3 is a top plan view of the orthopaedic instrument and femoral head shown in FIG. 2, illustrating the manner of use.

Referring now to FIG. 3, cap 14 includes a cap dome 38 rotatably received and retained in body 18 of head chuck 12. A handle 40 is disposed on dome 38 to aid in rotating cap 14. The underside of dome 38, relative to handle 40, includes a spiral thread 42 positioned for engagement with rack elements 26, 28 and 30. Thereby, rotation of cap 14, when engaged with rack elements 26, 28 and 30, causes locator devices 20, 22 and 24 to move equally inwardly or outwardly with respect to head chuck 12, depending on the direction of rotation of cap 14.

Orientation arm 16 is sufficiently long to reach the posterior portion of the femur, when head chuck 12 is disposed on and about a femoral head. Orientation arm 16 defines a plurality of reference indicia against which bone markings can be made and gauged on the posterior portion of the femur. In the embodiment shown, orientation arm defines a longitudinal slot 44 disposed substantially along the center line of orientation arm 16 throughout a substantial portion of the length of orientation arm 16. A plurality of edge notches 46, 48, 50, 52, 54 and 56 are defined by and disposed along the peripheral edges of orientation arm 16. A plurality of internal notches 58, 60, 62, 64, 66 and 68 are defined by and disposed along longitudinal slot 44. Edge notches 46, 48, 50, 52, 54 and 56 and internal notches 58, 60, 62, 64, 66 and 68 are arranged in groups such that four of such notches are provided in a group, in linear alignment. Thus, edge notches 46 and 52 are linearly aligned with internal notches 58 and 64. Similarly, edge notches 48 and 54 are linearly aligned with internal notches 60 and 66. Edge notches 50 and 56 are linearly aligned with internal notches 62 and 68. It should be understood that more or fewer notches may be provided for convenient marking.

Figure 2:
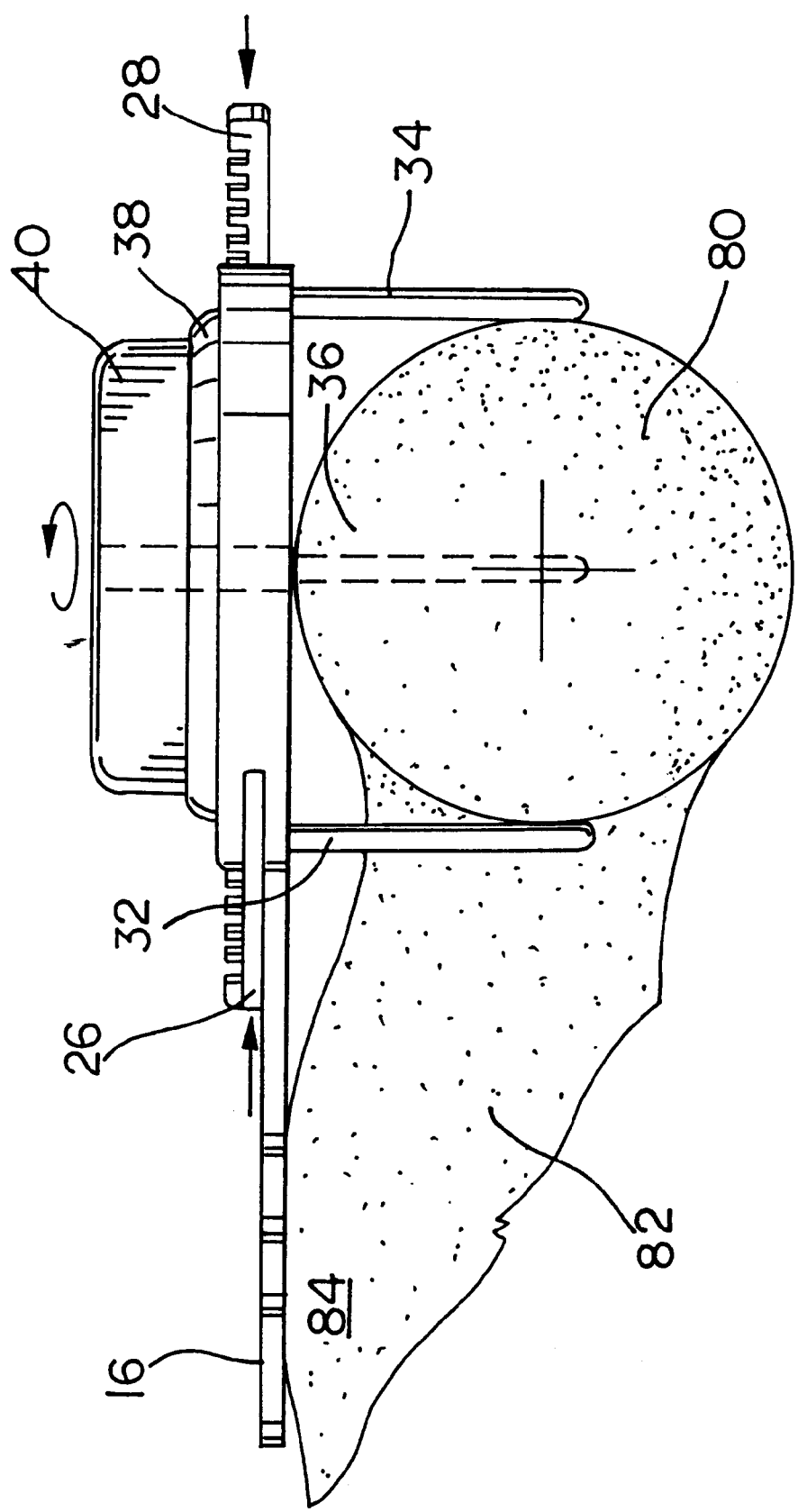
FIG. 2 is side elevational view of the orthopaedic instrument shown in FIG. 1, illustrating the manner of using the same on a femoral head.

Referring now to FIG. 2 through FIG. 5, the manner of use of the present invention will be described. The hip joint is exposed and prepared, surgically, in conventional manner. Prior to removal of femoral head 80 from proximal femur 82, head center instrument 10 is utilized to establish reference markings or landmarks relating to the pre-surgical joint geometry, which is to be duplicated in the subsequent implant of the prosthesis. Instrument 10 is positioned with head chuck 12 generally over femoral head 80 (FIG. 2). Locator pins 32, 34 and 36 are positioned outwardly of femoral head 80, and cap 14 is rotated, with appropriate adjustment or positioning of head chuck 12, until all locator pins 32, 34 and 36 are in contact with femoral head 80, and orientation arm 16 extends toward and over a portion of the posterior femur 84. Since rotation of cap 14, and spiral thread 42 engaged with rack elements 26, 28 and 30, moves each locator pin 32, 34 and 36 equally, head chuck 12 will center itself on femoral head 80.

Three reference markings 90, 92 and 94 are scribed onto posterior femur 84, such as by cautery or the like, using orientation arm 16 as a stencil for an appropriate marking device 120. Each of reference markings 90, 92 and 94 is a cross or "f" (FIG. 3). Reference markings 90 and 94 are scribed along the outer edges of orientation arm 16, and reference marking 92 is scribed within longitudinal slot 44, as shown in FIG. 3. Outer reference markings 90 and 94 are formed by scribing lines 90a and 94a, respectively, along the peripheral edges of orientation arm 16. Reference markings 90 and 94 are completed by scribing lines 90b and 94b, respectively, substantially perpendicular to lines 90a and 94a at aligned notches 48 and 54. The inner reference marking 92 is formed by scribing a line 92a within longitudinal slot 44, and is completed with a line 92b perpendicular to line 92a scribed between internal notches 60 and 66. Lines 90a, 92a and 94a are representative of and related to the neck angle of femoral head 80. Lines 90b, 92b and 94b are representative of and related to the neck length of femoral head 80. It should be understood that the selection of the appropriate notches at which to make the lines 90b, 92b and 94b, and the location along orientation arm 16 at which to scribe the lines 90a, 92a and 94a are a matter of surgeons choice, based on convenience of location for viewing the markings 90, 92 and 94 after reduction of femoral head 80.

Figure 4:
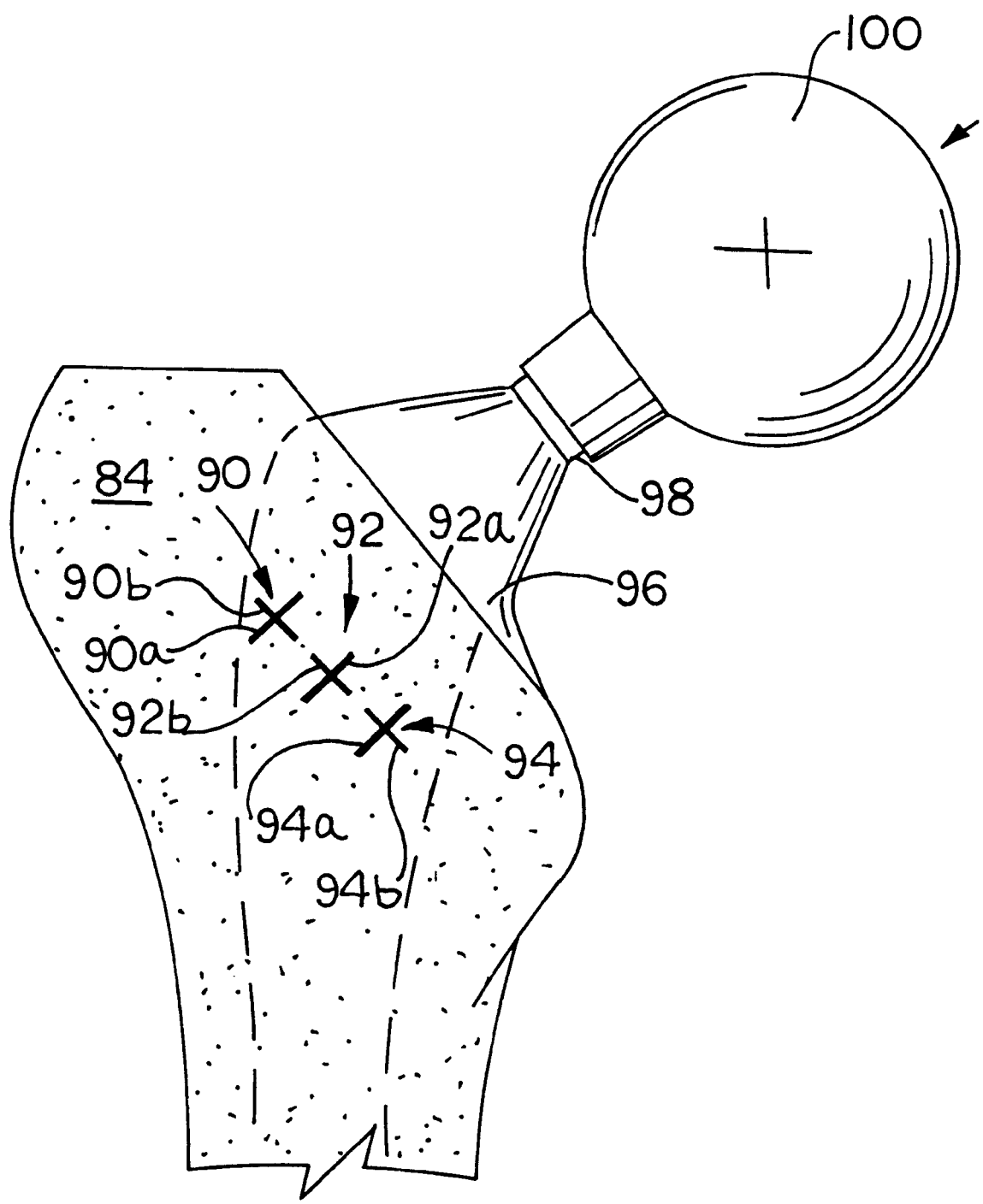
FIG. 4 illustrates a prosthetic femoral head positioned on the proximal end of a femur.
Figure 5:
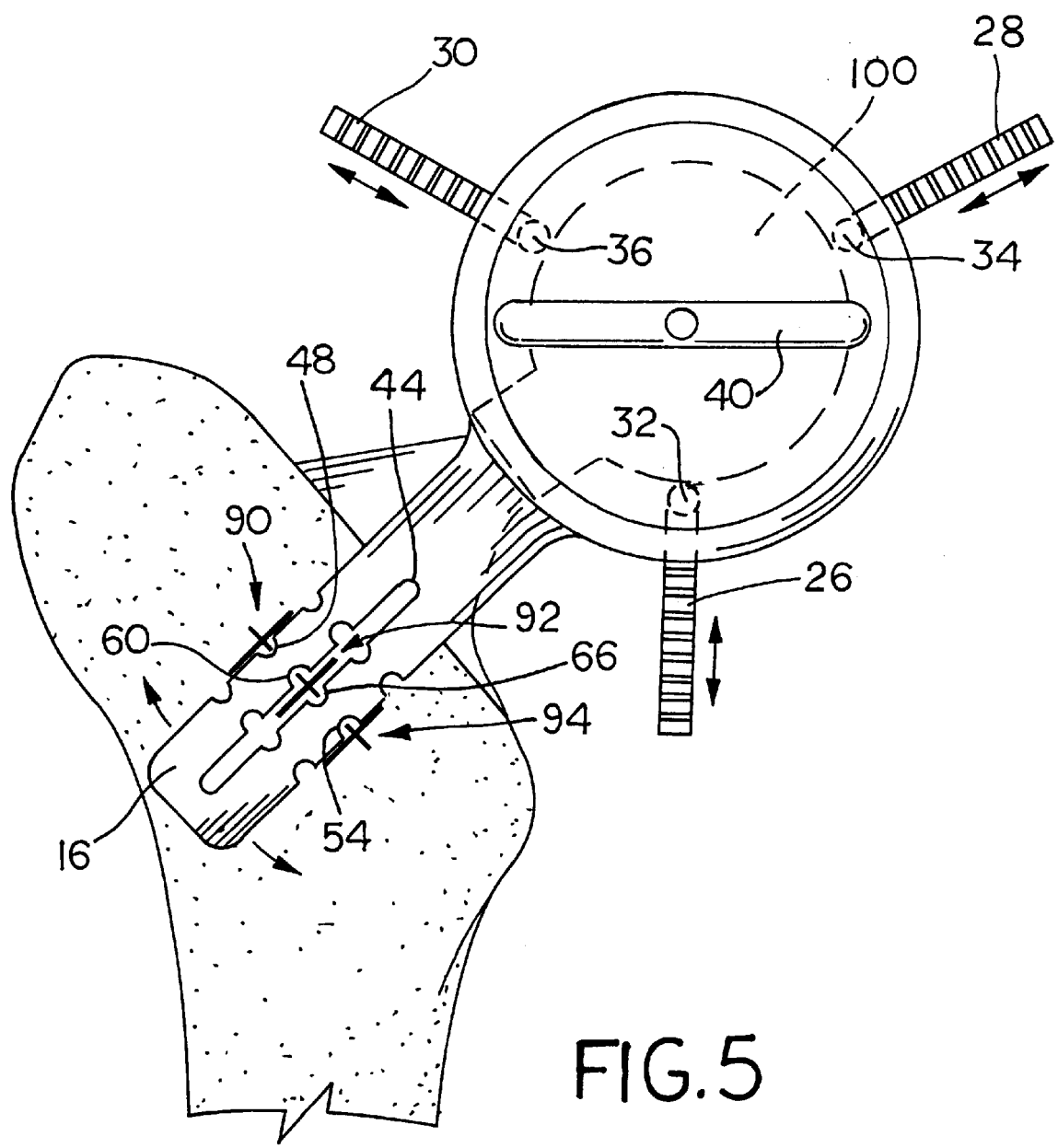
FIG. 5 is a top plan view similar to that of FIG. 3, but showing the orthopaedic instrument positioned relative to the prosthetic femoral head.

After scribing reference markings 90, 92 and 94 on posterior femur 84, head center instrument 10 is removed by rotating cap 14 to move pins 26, 28 and 30 outwardly, releasing head chuck 12 from femoral head 80. The hip joint replacement surgery continues in conventional manner. Femoral head 80 is reduced, the proximal femur is conventionally prepared, and a femoral implant stem 96 is inserted in the prepared intramedullary canal (FIG. 4). Femoral implant stem 96 includes a neck 98. A provisional head 100 is placed on neck 98. At this stage of the procedure, head center instrument 10 is used to verify that the neck length and neck angle selected for the implant are correct, to duplicate the pre-surgical joint geometry in the post-surgical geometry. Instrument 10 is positioned with head chuck 12 generally over provisional head 100 (FIG. 5). Locator pins 32, 34 and 36 are positioned outwardly of provisional head 100, and cap 14 is rotated with appropriate adjustment or positioning of head chuck 12 until all locator pins 32, 34 and 36 are brought into contact with provisional head 100, and orientation arm 16 extends toward and over the portion of the posterior femur 84 bearing markings 90, 92 and 94. Before orientation arm 16 is tightly engaged with provisional head 100, orientation arm 16 is rotated about provisional head 100 until cautery lines 90a, 92a and 94a are parallel to orientation arm 16, indicating proper neck angle adjustment. Final adjustment of rack elements 26, 28 and 30 is made by rotating cap 14, thereby centering head chuck 12 on provisional head 100. With locator pins 32, 34 and 36 tightened securely against provisional head 100, proper neck length is verified by establishing that cautery lines 90b, 92b and 94b are in the same ones of edge notches 46, 48, 50, 52, 54 and 56 and of internal notches 58, 60, 62, 64, 66 and 68 as used to make the original markings, before femoral head reduction. In the example shown, the neck length of the implant is proper when lines 90b, 92b and 94b are again lined up with notches 48, 54, 60 and 66. When all lines 90a, 92a, 94a, 90b, 92b and 94c of markings 90, 92 and 94 align with the indicia on orientation arm 16 in the same manner as when markings 90, 92 and 94 were scribed, the center of provisional head 100 is located in precisely the same position relative to proximal femur 82 as was the center of natural femoral head 80, pre-surgically. If cautery markings 90, 92 and 94 are not similarly located with respect to orientation arm 16 as each of the markings was when made, the provisional neck length and implant size can be varied until the proper orientation is achieved. For example, different neck lengths 98a, 98b, 98c can be provided, as shown by the dotted lines in FIG. 6, to increase or decrease the implant neck length. Thereafter the hip replacement surgical procedure continues conventionally. In a preferred embodiment, the first notches 50, 62, 68, 56; the second notches 48, 60, 66, 54; and the third notches 46, 58, 64, 52 would be spaced apart along the arm 16 a distance corresponding to the different neck lengths 98a, 98b, 98c. Thus, if cautery marks 90b, 92b, 94b are not aligned with the same notches as when the natural femoral head 80 was measured, an indication of the amount of neck length change is indicated.

The size of head chuck 12, the lengths of rack elements 26, 28 and 30, the lengths of locator pins 32, 34 and 36 and the length and arrangement of orientation arm 16, including the various reference indicia provided thereon, can be varied, as appropriate for an instrument 10 suitable for the size and type of joint on which instrument 10 is to be used. The basic concepts of the present invention, including the establishment of bone markings relating geometrical relationships to the head center of a ball joint, and the comparison of the same relationships following joint replacement procedures, can be applied on instruments for other types of joints as well, such as, for example, on a humerus.

While this invention has been described as having a preferred design and surgical procedure, the present invention can be further modified within the spirit and scope of this disclosure. While the invention has been described with respect to hip replacement surgery, it should be recognized that the head center instrument and its procedure of use may be utilized for the replacement of other ball components in ball and socket joints, such as those found in the human shoulder.

What is claimed is:

1. An orthopaedic instrument for establishing reference markings relating to the position of a ball in a ball joint, and for evaluating the positioning of a prosthetic implant replacing said ball, said instrument comprising:

an instrument head chuck;

a plurality of locator devices adjustably received by said head chuck and adapted to at least partially engage the ball;

adjustment means associated with said head chuck and said plurality of locator devices for bringing each one of said plurality of locator devices into engagement with the ball, and for securing the position of said head chuck relative to the ball; and an orientation arm extending outwardly from said head chuck, said orientation arm including reference indicia for establishing and comparing bone markings.

2. The orthopaedic instrument of claim 1, in which said plurality of locator devices includes a plurality of rack elements having rack teeth thereon; and a locator pin extending downwardly from each of said rack elements.

3. The orthopaedic instrument of claim 2, in which said head chuck includes a cylindrical body; a rotatable cap retained in said body; and a spiral thread disposed on said rotatable cap; said spiral thread engaging said rack teeth of said rack elements.

4. The orthopaedic instrument of claim 3, in which said orientation arm defines a longitudinal slot and a plurality of notches as reference indicia for establishing the location for making one or more bone markings, and against which bone markings are compared following prosthetic implant.

5. The orthopaedic instrument of claim 1, in which said orientation arm defines a longitudinal slot and a plurality of notches as reference indicia for establishing the location for making one or more bone markings, and against which bone markings are compared following prosthetic implant.

6. The orthopaedic instrument of claim 1, in which said orientation arm defines a plurality of openings therein, said openings defining a reference scale against which bone markings may be made and compared.

7. The orthopaedic instrument of claim 6, in which said orientation arm defines a central slot thereon.

8. The orthopaedic instrument of claim 7, in which said orientation arm defines a plurality of notches on the peripheral edge thereof.

9. The orthopaedic instrument of claim 8, in which said orientation arm defines in said central slot a plurality of notches extending therefrom.

10. The orthopaedic instrument of claim 9, in which one or more of said notches on the peripheral edge of said orientation arm align with one or more of said notches extending from said central slot.

11. A method for comparing the neck angle and length of a prosthetic ball component of a ball joint to the neck angle and length of the natural ball, comprising:
providing an instrument having a head chuck adapted to be secured in position relative to the ball of a ball joint and of a prosthetic implant;
providing an arm on said instrument extending from said head, said arm being of a length to reach a surface area of the bone remaining after surgical reduction;
providing a plurality of reference indicia on said arm of said instrument;
exposing the natural ball component of the ball joint;
affixing said arm relative to the center point of the ball component;
establishing bone markings relative to specific ones of said plurality of indicia on the orientation arm;
removing the arm;
replacing, surgically, the natural ball component with a prosthetic ball component;
securing the orientation arm relative to the center point of the prosthetic ball;
comparing the bone markings to the indicia on the orientation arm; and
adjusting, as necessary, the neck length and angle of the prosthetic ball to match said bone markings against said specific ones of said plurality of indicia against which said bone markings were made.

12. The method of claim 11, further comprising the steps of providing a plurality of adjustable locator pins on said head chuck; adjusting said locator pins to at least partially engage the natural ball during said affixing step, disengaging said locator pins from the natural ball after completing said establishing bone markings; and adjusting said locator pins to at least partially engage said prosthetic ball during said step of securing the orientation arm relative to the center point of the prosthetic ball.

13. The method of claim 12, further comprising operating rack elements simultaneously to adjust said locator pins during said affixing and securing steps.

14. The method of claim 13, further comprising rotating a spiral thread engaged with the rack elements.

15. The method of claim 14, wherein said step of establishing bone markings includes creating cautery lines relative to specific ones of said plurality of indicia on said arm.

16. The method of claim 11, wherein said step of establishing bone markings includes creating cautery lines relative to indicia on said orientation arm.

17. An orthopaedic instrument comprising:
a head chuck for engaging a ball of a ball joint, said head chuck including a cylindrical body and a cap rotatably secured in said body;
an orientation arm extending radially outwardly from said body;
a plurality of locator devices associated with said head chuck for securing said head chuck relative to the center point of a ball component in a ball joint; and
indicia on said orientation arm having reference points for making markings.

18. The orthopaedic instrument of claim 17 wherein said orientation arm defines a plurality of openings as a stencil at which bone markings can be made, and against which existing bone markings can be compared.

19. The orthopaedic instrument of claim 18, including a plurality of rack elements adjustably secured in said body, and a driver for said rack elements.

20. The orthopaedic instrument of claim 19, wherein said driver includes a spiral thread on said cap, said spiral thread being engaged with said rack elements.

21. A method for replacing a femoral head, comprising;
exposing the femoral head surgically;
securing a reference gauge against the posterior femur relative to the femoral head center;
creating reference bone markings on the posterior femur;
removing the reference gauge;
replacing the femoral head with a prosthetic femoral head;
re-securing the reference gauge against the posterior femur relative to the center of the prosthetic femoral head;
comparing the bone markings against the reference gauge; and
adjusting the prosthetic femoral head to achieve a relationship between the and the reference gauge similar to the relationship when said bone markings were made.

22. The method of claim 21, including operating rack elements to engage and disengage said reference gauge relative to the femoral head and the prosthetic femoral head.

23. The method of claim 22, including rotating a spiral thread engaged with said rack elements.

* * * * *